United States Patent [19]

Fridovich et al.

[11] Patent Number: 5,223,538

[45] Date of Patent: Jun. 29, 1993

[54] SUPEROXIDE DISMUTASE MIMIC

[75] Inventors: Irwin Fridovich, Durham; Douglas J. Darr, Timberlake, both of N.C.

[73] Assignee: Duke University, Durham, N.C.

[21] Appl. No.: 32,475

[22] Filed: Mar. 31, 1987

[51] Int. Cl.$^5$ .................... A61K 31/16; A61K 37/50; C12N 9/02

[52] U.S. Cl. .................... 514/616; 424/94.4; 424/DIG. 6; 435/184

[58] Field of Search ........ 435/189; 424/94.4, DIG. 6; 514/616, 516; 564/153

[56] References Cited

U.S. PATENT DOCUMENTS

| | | | |
|---|---|---|---|
| 4,172,072 | 10/1979 | Ashmead | 260/115 |
| 4,216,143 | 8/1980 | Ashmead | 260/113 |
| 4,346,174 | 8/1982 | Yasuda | 435/189 |
| 4,530,963 | 7/1985 | Devoe et al. | 525/54.1 |
| 4,758,422 | 7/1988 | Quay | 424/9 |

OTHER PUBLICATIONS

Plowman, J. E. et al. (1984) J. Inorg. Biochem. 20(3), 183.
Rabinowitch, H. D., et al. (1987) Free Radical Biology & Medicine 3, 125–131.
Archibald et al; Archives of Biochemistry and Biophysics, vol. 215, No. 2, May, 1982; pp. 589–596.
Archibald et al; Archives of Biochemistry and Biophysics, vol. 214, No. 2, Apr. 1, 1982; pp. 452–463.
Archibald; Copyright 1983 by Elsevier Science Publishing Co., Inc., Gerald Cohen and Robert A. Greenwald, Editors, "Oxy Radicals & Their Scavenger Systems", vol. 1, Molecular Aspects, pp. 207–217.
Chemical Abstracts; vol. 68, No. 15, Apr. 8, 1968–67581n.
Chemical Abstracts: vol. 99, No. 20, Nov. 14, 1983–164612w.
Chemical Abstracts, vol. 96, No. 23, Jun. 7, 1982–195506g.
Chemical Abstracts, vol. 95, No. 9, Aug. 31, 1981–76615m.
Epp et al; 1986 Elsevier Science Publishers B. V. (Biomedical Division) Superoxide and Superoxide Dimutase in Chemistry, Biology and Medicine; G. Rotilio, editor pp. 76–78.
Yamaguchi et al; FEBS 3451, vol. 197, No. 1,2; mar. 1986, pp. 249–252.
Koppenol et al; Archives of Biochemistry and Biophysics, vol. 251, No. 2, Dec., 1986, pp. 594–599.
P. Simon; The Lancet, Aug. 27, 1983; pp. 512–513; Desferrioxamine, Ocular Toxicity and Trace Metals.
Fridovich, "Natural and Synthetic Defenses Against Oxygen Radicals", Environs, Dec. 1986, pp. 2–3.

*Primary Examiner*—Charles L. Patterson, Jr.
*Attorney, Agent, or Firm*—Cushman, Darby & Cushman

[57] ABSTRACT

The invention relates to a water-soluble complex formed between a chelating agent and manganese and pharmaceutical compositions thereof. The complex is a low molecular weight mimic of superoxide dismutase. The invention further relates to a method of using the complex comprising treating plant and animal cells with an amount of the complex sufficient to reduce or prevent superoxide radical-induced toxicity.

8 Claims, 1 Drawing Sheet

SUPEROXIDE DISMUTASE MIMIC

BACKGROUND OF THE INVENTION

1. Technical Field

The invention relates, in general, to a low molecular weight mimic of superoxide dismutase and, in particular, to a desferrioxamine-manganese complex capable of scavenging superoxide radicals.

2. Background Information

The superoxide radical ($O_2^-$) can be generated within living cells during both enzymic and non-enzymic oxidations. Because of the direct reactivity of $O_2^-$, and the reactivity of secondary free radicals that it can generate, $O_2^-$ presents a threat to cellular integrity. This threat is met by a family of defensive enzymes that catalyze the conversion of $O_2^-$ to $H_2O_2+O_2$. These enzymes, superoxide dismutases (SOD), react with $O_2^-$ at a rate that approaches the theoretical diffusion limit and appear to be important for aerobic life. The $H_2O_2$ generated by SOD is disposed of either by catalytic conversion to $O_2$ and $H_2O$ by catalases, or by reduction to water at the expense of thiol, amine or phenolic substrates by peroxidases.

The superoxide radical has been shown to be an important causative factor in the damage resulting from: a) autoxidation; b) oxygen toxicity; c) the oxygen-dependent toxicity of numerous compounds; d) reperfusion injury; e) inflammation; and f) frostbite; and is implicated in the limited viability of transplanted organs and tissues.

The earliest work bearing on the functions of SOD dealt primarily with oxygen toxicity and with the oxygen-dependent toxicities of viologens, quinones and related redox-cycling compounds. These investigations established that $O_2^-$, made within cells, can kill the cells and that SOD provides a defense It is now known that $O_x^-$ is not only an unwanted and dangerous by-product of dioxygen metabolism, but is also produced in large quantities by certain specialized cells, seemingly to serve a specific purpose. Neutrophils, and related phagocytic leucocytes, contain a membrane-associated NADPH oxidase that is activated when the cells are stimulated and that specifically reduces dioxygen to $O_2^{31}$. A defect in this enzyme weakens the microbicidal activity of these leucocytes, leading to chronic granulomatous disease.

The known association of neutrophils with the inflammatory process, and the production of $O_2^-$ by activated neutrophils, suggests a role for $O_2^-$ in the development, and possibly in the deleterious consequences, of inflammation. An enzymic source of $O_2^-$ decreases the viscosity of synovial fluid by depolymerizing hyaluronate and SOD exerts a protective effect. Injecting an enzymic source of $O_2^-$, such as xanthine oxidase, causes a localized inflammation that can be prevented by scavengers of oxygen radicals, such as SOD.

The anti-inflammatory effect of SOD, noted in model inflammations in laboratory animals, is explained in terms of the inhibition of the production of a neutrophil chemotaxin by the reaction of $O_2^-$ with a precursor present in normal human serum. SOD, when injected into the circulation, is rapidly removed by the kidneys, such that the circulation half life of i.v.-injected bovine SOD in the rat is only 7 minutes. This can be markedly increased by coupling the SOD to polyethylene glycol or ficoll, with a corresponding increase in anti-inflammatory effect.

The tissue damage that develops as a consequence of temporary ischemia has classically been attributed to the lack of ATP which develops during the hypoxia imposed during ischemia. Data support the view that this damage actually occurs during reperfusion and is an expression of increased oxygen radical production. SOD protects against this reperfusion injury.

The mechanism which best fits these data depends upon degradation of ATP to hypoxanthine and upon the conversion of xanthine dehydrogenase to xanthine oxidase, during the period of ischemia. Reperfusion then introduces dioxygen, which is reduced to $O_2^-$ by the action of xanthine oxidase on the accumulated hypoxanthine. As expected from this model, allopurinol, which inactivates xanthine oxidase, also protects against reperfusion injury.

The superoxide dismutases are used as pharmacological agents. They are applied to the treatment of inflammatory diseases and are being investigated in the cases of the reperfusion injury associated with skin grafts, organ transplants, frostbite and myocardial infarction. Size, antigenicity and cost, however, mitigate against their widespread usage. Since the enzyme must be isolated from biological sources, it is in limited supply, very expensive and plagued by problems caused by contaminants.

It has long been apparent that low molecular weight mimics of SOD, capable of acting intracellularly, would be useful. Manganese(II), per se, will scavenge $O_2^-$ and, in suitable buffers, will do so catalytically. However, Mn(II) binds avidly to a number of proteins and in so doing loses its activity. Cu(II) is itself a very effective catalyst of the dismutation of $O_2^-$. Since the first SOD to be discovered was a copper protein, copper-complexes have been examined for SOD activity. The problems with free Cu(II) are that it readily forms a hydroxide and that it binds strongly to many macromolecules. For these reasons Cu(II) per se is most active in acid solutions and in the absence of strongly binding ligands. Among the complexes of Cu(II), the SOD-like activity for which have been reported, are: Cu(lys)2 and Cu(gly-his)2, Cu(diisopropylsalicylate)2, Cu(penicillamine), Cu(histidine), Cu(dipeptides) and Cu(gly-his-lys). There are serious problems with all of these copper complexes. Many are, in fact, merely acting as metal buffers, serving to solubilize the Cu(II) and are of insufficient stability to retain activity in the presence of serum albumin. Investigations of Cu(II) complexes have thus far not resulted in the discovery of any biologically useful mimics of SOD.

SUMMARY OF THE INVENTION

It is an object of the invention to provide an inexpensive, synthetic, low molecular weight mimic of SOD.

It is a further object of the invention to provide a scavenger of superoxide radicals that is not inactivated by proteins.

It is another object of the invention to provide a method of using a low molecular weight mimic of SOD to reduce or prevent the toxicity of superoxide radical-induced toxicity.

It is a further object of the invention to provide a pharmaceutical composition containing, as an active ingredient, a stable, low molecular weight mimic of superoxide dismutase.

Further objects and advantages of the present invention will be apparent from the following detailed description thereof.

The invention relates to a low molecular weight mimic of superoxide dismutase comprising a water-soluble complex formed between a chelating agent, for example, desferrioxamine or analogs or derivatives thereof, and manganese. The mimic, designated DF-Mn when it comprises desferrioxamine and manganese, catalyzes the dismutation of $O_2^-$, and retains its activity in the presence of serum albumin and cellular extracts containing protein. It is anticipated that the mimic, and pharmaceutical compositions thereof, will be useful in the following situations: 1) treating inflammation; 2) extending the storage lifetime of organs and tissues intended for transplantation; 3) decreasing damage to the heart suffered as a consequence of infarction; 4) protecting against tissue death and necrosis following any situation entailing temporary cessation of circulation to a tissue or organ; 5) as a radioprotectant; and 6) as an antioxidant applicable to any free radical chain oxidation in which $O_2^-$ serves either as initiator or chain propagator. It is also anticipated that the mimic will be useful in inhibiting autoxidation reactions, thus providing increased shelf life for food products, pharmaceuticals, and stored blood, etc.

DETAILED DESCRIPTION OF THE INVENTION

Figure 1:
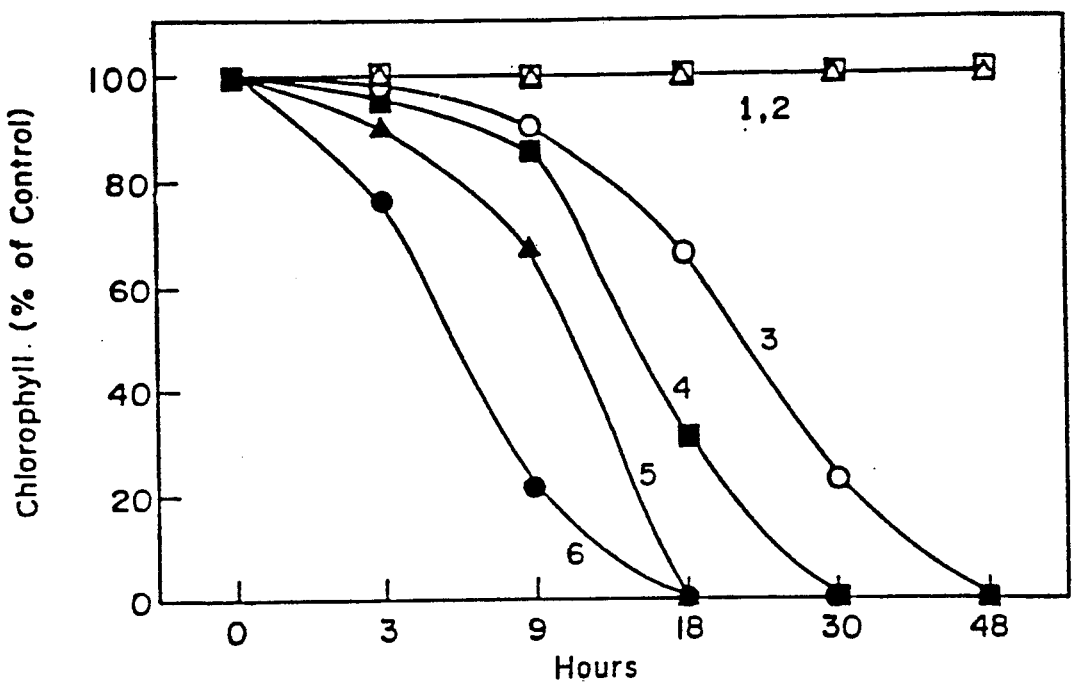
FIG. 1 - Bleaching of chlorophyll in *D.salina* by paraquat.

According to the present invention there is provided a low molecular mimic of SOD comprising a water-soluble complex formed between a chelating agent and manganese. Chelating agents employed are, advantageously, siderophores, advantageously, of the hydroxamate type, or analogs or derivatives thereof (for review see Neiland, J. B., Inorganic Biochemistry, Eichhorn, G., Ed., Elseiver, Amsterdam, 1973). Suitable hydroxamate-type siderophores include, but are not limited to, schizokinen, hadacidin, rhodotorulic acid, ferrichrome, aspergillic acid and, advantageously, desferrioxamine.

The manganese present in the water-soluble complex has an effective valence of four. The term "effective valence of four" is used to indicate that the manganese present in the complex is that derived either from reacting a chelating agent with a manganese(IV) salt, advantageously, $MnO_2$, or from reacting a chelating agent with a manganese(II) salt, advantageously, $MnCl_2$, which latter reaction is carried out, advantageously, in a neutral oxygenated aqueous solution such that autoxidation of the manganese occurs. It is also contemplated that the above-described water soluble complex comprising a chelating agent and manganese having an effective valence of four, may be derived by reacting a manganese salt, in which salt manganese has a valence of III, V, VI or VII, with a chelating agent under such conditions that the above-described water-soluble complex in which complex manganese has an effective valence of four, is formed.

In one embodiment of the present invention, the complex is that prepared by combining $MnO_2$, advantageously, in approximately 10 percent molar excess, with desferrioxamine, or analogs or derivatives thereof, advantageously, at a concentration of approximately 50 mM, in deionized water or a suitable buffer having a pH of approximately 6 to 8. After stirring until the reaction is complete, that is, advantageously, approximately 12 hours at approximately 25° C. or approximately 6-8 hours at approximately 50° C., residual $MnO_2$ is removed, advantageously, by centrifugation or filtration, leaving a green supernatant solution containing essentially pure DF-Mn.

The complex between a chelating agent and manganese, advantageously DF-Mn, mimics the catalytic activity of native SOD, that is, it is capable of catalyzing the dismutation of $O_2^-$ into $H_2O_2$ and $O_2$, and it is capable of retaining its activity in the presence of serum albumin, total serum or whole bacterial cell extracts. One micromolar DF-Mn exhibits one unit of SOD activity in the xanthine oxidase cytochrome c assay (McCord, J. M. and Fridovich, I. (1969) J. Biol. Chem. 244: 6049-6055). DF-Mn is stable to dilution and to elevated temperatures, that is, of approximately 50° C. An increase in the catalytic activity of DF-Mn, approximately four fold, is achieved by heating the complex, advantageously, at a temperature of approximately 100° C. for approximately 15 minutes. The increase in catalytic activity of DF-Mn achieved by such heating is attributable to a physical change in the complex as evidenced by a change in the color of the solution, that is, the solution which is green prior to heating, becomes gold after the heating process.

The invention contemplates a method of protecting both plant and mammalian cells from the toxicity of superoxide radicals comprising treating the cells with an amount of the above-described water-soluble complex, that is, the complex formed between a chelating agent, advantageously, desferrioxamine or analogs or derivatives thereof, and manganese, sufficient to reduce or prevent superoxide radical-induced toxicity, which complex is capable of catalyzing the dismutation of superoxide radicals and which complex is capable of retaining its activity in the presence of proteins. The complex, advantageously DF-Mn, can be used to protect against the reperfusion injuries encountered during or following: a) organ transplant, b) frostbite; c) angioplasty; d) the administration of streptokinase or tissue plasminogen activator following myocardial infarction. The complex, advantageously DF-Mn, can be used to protect against inflammatory diseases or swelling encountered during or following: a) head injury; b) temporary ischemia to the brain; c) inflammatory joint diseases; and d) gouty attacks. The complex, advantageously DF-Mn, can be used to protect red blood cells in anemia and to prevent rejection of transplanted organs. The complex, advantageously DF-Mn, can be used to inhibit the formation of DNA-breaking clastogenic factor in autoimmune disease.

The complex, advantageously DF-Mn, can be used as a catalytic scavenger of superoxide radicals to provide protection against or treatments for: oxygen toxicity; the oxygen-dependent toxicities of viologens, quinones and related compounds in plants and animals; the very limited storage viability of transplanted hearts, kidneys, skin and other organs and tissues; protection against damage caused by all forms of electromagnetic radiation including visible light, ultraviolet light and ionizing radiation; slowing of the aging process; and protection against the oxygen-dependent toxicities of a variety of redox-active drugs and environmental pollutants.

The invention also contemplates a method of inhibiting damage due to autoxidation of substances resulting in the formation of $O_2^-$ including food products, pharmaceuticals, stored blood, etc. The method comprises adding to food products, pharmaceuticals, stored blood and the like, an amount of the complex, advantageously, DF-Mn, sufficient to inhibit or prevent oxidation damage and thereby to inhibit or prevent the degradation associated with the autoxidation reactions.

It will be clear to one of ordinary skill in the art that the amount of the complex, advantageously DF-Mn, to be used in a particular treatment or to be associated with a particular substance can be determined by one of ordinary skill in the art by routine trials.

The invention further contemplates a pharmaceutical composition comprising, as an active ingredient, the above-described complex, that is, the water-soluble complex formed between a chelating agent, advantageously, desferrioxamine or analogs or derivatives thereof, and manganese, which complex is capable of catalyzing the dismutation of superoxide radicals and which complex is capable of retaining its activity in the presence of proteins, which complex is present in an amount sufficient to reduce or prevent superoxide radical-induced toxicity, together with a pharmaceutically acceptable solid or liquid carrier, diluent or excipient thereof. The composition may take any of the conventional forms for effective administration, e.g., pills, tablets, sterile injectable solutions and the like. When the composition is administered orally, it must be suitably coated, by any of the known techniques, so that it is protected as it passes through the acid environment of the stomach. The composition may also take any of the conventional forms for topical application, e.g, creams, lotions and the like.

The invention is illustrated by way of the following non-limiting examples:

EXAMPLE 1

Catalytic Activity of DF-Mn in the Presence of Protein

Using the cytochrome c reduction assay (McCord, J. M. and Fridovich, I. (1969) J. Biol. Chem. 244; 6049-6055) in the presence of increasing amounts of serum albumin, total serum or whole bacterial cell extracts, a 1 μM solution of DF-Mn exhibited one unit (defined in above reference) of SOD activity.

EXAMPLE 2

Catalytic Activity of Rhodotorulic Acid and Manganese

A complex was formed by reacting rhodotorulic acid with $MnCl_2$ in a ratio of 1:1 in a neutral, oxygenated aqueous solution. The pH was adjusted to 8. A 1 μM solution of the complex had approximately 1 unit of SOD activity as assayed using the cytochrome c reduction assay.

Rhodotorulic acid was also reacted with $MnO_2$. A colored complex was formed.

EXAMPLE 3

Protection of Mammalian Cells Against Oxygen Toxicity by DF-Mn

Chinese hamster ovary cells were exposed to paraquat (200 μM), a compound known to form $O_2^-$ intracellularly. After an eight-hour exposure, 50 to 70% cell death was observed. Pretreatment with 20 μM DF-Mn reduced cell death by 70±9% (mean±SD; N=8 experiments). Desferrioxamine, manganese (chloride or dioxide), or EDTA-Mn alone at 20 μM gave little or no protection. Native Cu-Zn SOD was also less effective, presumably because it could not enter the cells. Copper-DIPS gave approximately 30% protection when present at levels exhibiting 10 times the "SOD" activity of DF-Mn. The data indicate that DF-Mn can enter mammalian cells and afford protection against paraquat-mediated damage.

EXAMPLE 4

Protection by DF-Mn Against Damage to Mammalian Lenses by Superoxide Radicals Generated During Cyclic, Oxidation-reduction of Redox Compounds Fresh lenses of rabbits were incubated in Krebs-Ringer medium with Hepes buffer (pH 7.4) and 5 mM glucose at 37° C. for 3 hours. Malondialdehyde, a marker of lens damage, was 1.16±0.12 nmole/g wet weight in control lenses. This increased 6-8 fold ($p<0.001$) in the presence of 1 mM paraquat, diquat, plumbagin or juglone. In such lenses, reduced glutathione (GSH) was decreased 30-55% as compared to 8.74±0.12 μmole/g wet weight in lenses incubated in the absence of these compounds. Under identical experimental conditions, other protein-SH of lenses were not significantly altered. AMM, a liposomal superoxide dismutase (Michelson, A. M., Puget, K , Durosan, P. (1981), Molec. Physiol. 1:85-96) or 1 mM DF-Mn significantly prevented these changes to the lens. The involvement of oxygen radicals in the toxicity of these redox compounds is evidenced by the fact that lenticular damage was potentiated in the presence of 100% $O_2$ as gas phase and negligible in 100% $N_2$.

EXAMPLE 5

Protection by DF-Mn of the Green Alga, Dunaliella Salina, from the Effects of Paraquat Experimental Conditions Culture Conditions: *Dunaliella salina* was cultivated phototrophically in mineral medium (J.Phycol.18:5-29-537 (1982)) with modification. The medium contained 0.3 mM $CaCl_2$; 2 μM $FeCl_3$; 20 μM EDTA; 0.1 mM $KH_2PO_4$; 5.0 mM $KNO_3$; 5 mM $MgSO_4$; 50 mM $NaHCO_3$; and 1.67 M NaCl. $FeCl_3$ and EDTA were premixed prior to being added to the medium. The pH of the medium was maintained at 6.8. Cultures were inoculated and allowed to grow for 2-3 days, aliquots were then placed on a gyrating platform for the experimental treatments. Illumination was provided by natural daylight supplemented by incandescent bulbs.

Assays: Algal cells were collected by centrifugation and chlorophyll was extracted by resuspension in N,N-dimethylformamide for 24 hours at 4° C. with occasional agitation. After clarification by centrifugation, the dissolved chlorophyll was estimated from measurements of absorbance at 664 and 647 nm (Plant Physiol. 65:478-479 (1980). Plant Physiol. 69:1376-1381 (1980)). Algal cultures, intended for assay of protein and of enzymic activities, were harvested by centrifugation during log phase and were washed by gentle resuspension in 50 mM potassium phosphate, 0.1 mM EDTA, pH 7.8, followed by centrifugation. The cells were resuspended in phosphate-EDTA buffer and were lysed by being passed through a French Pressure Cell. Lysates were clarified and the resultant soluble extracts assayed for protein, and for SOD (J. Biol. Chem. 244:6049-6055 (1969)) and catalase (J. Biol. Chem. 195:133-140 (1952)) activities.

Parquat and Electrophoresis: When the effects of paraquat were being investigated, the compound was added to cultures which had been growing for 48 hours and were still in log phase, the incubation was continued for 18 hours. The cells were assayed for chlorophyll content or for protein and enzymic activities as described above. Electrophoresis was performed on 7% polyacrylamide gels and duplicate electropherograms were stained for catalase (Anal. Biochem. 140:532–537 (1984)) or for SOD activities (Anal. Biochem. 44:276–278 (1971)).

EXPERIMENT

Figure 2:
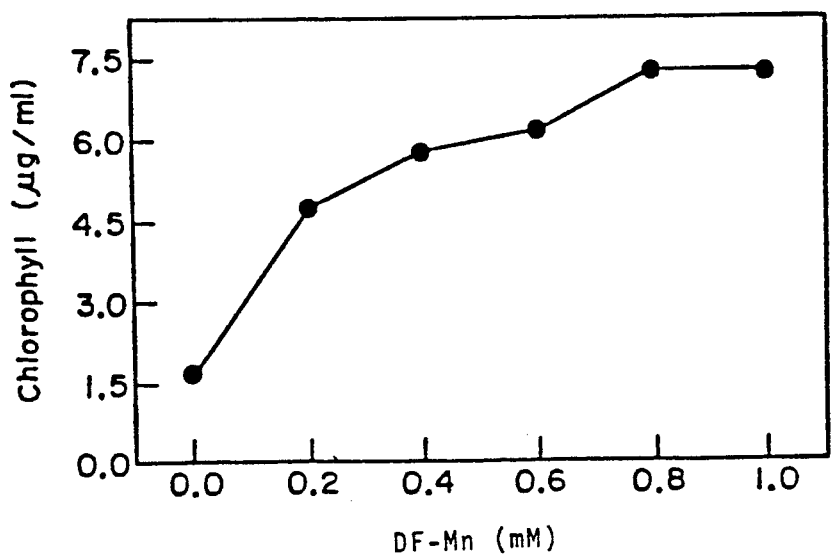
FIG. 2 - DF-Mn protection against paraquat.

Illuminated log phase cultures of *D. salina* were bleached when exposed to paraquat at, or exceeding, 250 μM. This progressive bleaching, shown in FIG. 1 (line 1=0.05 mM, line 2=0.10 mM, line 3=0.25 mM, line 4=0.5 mM, line 5=1.0 mM, line 6=1.5 mM), was accompanied by loss of motility observed under light microscope. DF-Mn, when present in the culture medium, protected against the bleaching effect of paraquat in a dose-dependent manner (FIG. 2). The protective effect of DF-Mn was not due to masking of incident light since at 634 nm the ratio of the absorbance of DF-Mn to that of chlorophyll was 0.1/0.731; while at 433 nm the ratio was 0.24/1.45.

The results in Table I indicate that DF-Mn exerts its protective effect very soon after being added to the medium. Since neither SOD nor catalase, added to the suspending medium, protected against the toxicity of paraquat (Tables II and III), it is apparent that scavenging of $O_2^-$ or of $H_2O_2$ in the medium is not an effective means of protection. Washing *D. salina* exposed to DF-Mn restores sensitivity towards paraquat, indicating that DF-Mn, having entered the cells, readily diffused out.

The protective effect of DF-MN is due to the complex itself rather than to the products of its dissociation. This is evidenced by the fact that desferrioxamine alone caused a progressive bleaching of the cultures in the absence of paraquat. Mn(II) or Mn(III)-pyrophosphate, failed to protect *D. salina* against the deleterious effects of paraquat. $MnO_2$ alone is essentially insoluble in water and had no effect on the bleaching of *D. salina* by paraquat.

The foregoing invention has been described in some detail by way of examples for purposes of clarity and understanding. It will be obvious to those skilled in the art from a reading of the disclosure that it is contemplated that the compound and composition thereof described herein will be used to inhibit the deleterious effects of superoxide radicals both in agricultural and clinical settings. Various combinations in form and detail can be made without departing from the scope of the invention.

TABLE I

| | Effect of DF-Mn on the Bleaching of *D. salina* by Paraquat | | |
|---|---|---|---|
| | Chlorophyll (μg/ml) | | Chlorophyll/Dry Weight (μg/mg) |
| Treatment | chl a | Total | Total |
| Control | 12.7 ± 0.6 | 17.1 ± 0.9 | 3.4 ± 0.4 |
| Paraquat[a] | 0.0 | 0.0 | 0.0 |
| DF-Mn[b] | 13 ± 1 | 17 ± 1.1 | 3.2 ± 0.3 |
| DF-Mn 30 min prior to paraquat | 6.6 ± 0.9 | 9.3 ± 1.3 | 1.9 ± 0.3 |
| DF-Mn 30 min following paraquat | 6.2 ± 0.8 | 9.0 ± 1.2 | 2.0 ± 0.3 |

[a]Paraquat was added to a final concentration of 1.0 mM.
[b]DF-Mn was added to a final concentration of 1.0 mM.

TABLE II

| | Effect of DF-Mn and of SOD on the Bleaching of *D. salina* by Paraquat | | |
|---|---|---|---|
| | Chlorophyll (μg/ml) | | Chlorophyll/Dry Weight (μg/mg) |
| Treatment | chl a | Total | Total |
| Control | 15.6 ± 1.2 | 20.2 ± 1.6 | 3.6 ± 0.4 |
| Paraquat[a] | 0.0 | 0.0 | 0.0 |
| DF-Mn[b] | 16.3 ± 0.8 | 21.3 ± 1.0 | 3.6 ± 0.4 |
| SOD[c] + paraquat | 0.0 | 0.0 | 0.0 |
| DF-Mn[b] + SOD | 16.6 ± 0.4 | 21.8 ± 0.3 | 4.0 ± 0.3 |
| DF-Mn + paraquat | 7.5 ± 1.1 | 10.8 ± 1.3 | 1.8 ± 0.2 |
| DF-Mn + SOD + paraquat | 8.8 ± 1.3 | 12.1 ± 1.8 | 2.0 ± 0.3 |

[a]Paraquat was added to 1.0 mM.
[b]DF-Mn was added to 1.0 mM.
[c]SOD was added to 10 μg/ml.

TABLE III

| | Effect of DF-Mn and Catalase on Bleaching of *D. salina* by Paraquat | | |
|---|---|---|---|
| | Chlorophyll (μg/ml) | | Chlorophyll/Dry Weight (μg/mg) |
| Treatment | chl a | Total | Total |
| Control | 17.2 ± 0.5 | 22.0 ± 0.6 | 4.0 ± 0.2 |
| Paraquat[a] | 0.0 | 0.0 | 0.0 |
| DF-Mn[b] | 16.0 ± 0.9 | 21.4 ± 0.8 | 3.8 ± 0.2 |
| DF-Mn + paraquat | 10.0 ± 0.2 | 13.6 ± 0.4 | 2.4 ± 0.1 |
| Catalase[c] + paraquat | 0.0 | 0.0 | 0.0 |
| DF-Mn + catalase | 18.1 ± 1.8 | 23.5 ± 2.0 | 4.2 ± 0.3 |
| DF-Mn + catalase + paraquat | 9.4 ± 0.9 | 13.0 ± 1.0 | 2.3 ± 0.2 |

[a]Paraquat was added to 1.0 mM.
[b]DF-Mn was added to 1.0 mM.
[c]Catalase was added to 10 μg/ml.

What is claimed is:

1. A method of protecting cells from the toxicity of superoxide radicals comprising treating said cells with an amount of a water-soluble complex formed between a chelating agent and manganese sufficient to reduce or prevent superoxide radical-induced toxicity, wherein said chelating agent is a hydroxamate-type siderophore, or analog or derivative thereof capable of forming said complex.

2. A method according to claim 1 wherein said cells are mammalian cells.

3. A method according to claim 1 wherein said cells are plant cells.

4. A method according to claim 1 wherein said chelating agent is desferrioxamine or analog or derivative thereof capable of forming said complex.

5. A method according to claim 1 wherein said manganese has an effective valence of four.

6. A method according to claim 1 wherein said superoxide-radicals are the result of reperfusion injuries.

7. A method according to claim 1 wherein said superoxide-radicals are the result of inflammatory diseases.

8. A method of inhibiting damage due to auto-oxidation of a substance with the subsequent formation of $O_2^-$ comprising adding to said substance an amount of a water soluble complex formed between a chelating agent and manganese sufficient to reduce or prevent oxidation damage, wherein said chelating agent is a hydroxamate-type siderophore, or analog or derivative thereof capable of forming said complex.

* * * * *

UNITED STATES PATENT AND TRADEMARK OFFICE
CERTIFICATE OF CORRECTION

PATENT NO. :       5,223,538
DATED      :       June 29, 1993
INVENTOR(S) :      FRIDOVICH et al It is certified that error appears in the above-indentified patent and that said Letters Patent is hereby corrected as shown below:

Column 1, line 39, change "$O_x^-$" to -- $O_2^-$ --;

Column 1, line 46, change "$O_2^{31}$" to -- $O_2^-$ --; and

Column 3, line 42, change "Elseiver" to --Elsevier--.

Signed and Sealed this

Twelfth Day of July, 1994

Attest:

BRUCE LEHMAN

*Attesting Officer*    *Commissioner of Patents and Trademarks*